United States Patent [19]
Kee

[11] Patent Number: 5,337,780
[45] Date of Patent: Aug. 16, 1994

[54] SUCTION CONTROL VALVE

[75] Inventor: Kok-Hiong Kee, St. Louis, Mo.

[73] Assignee: Sherwood Medical Company, St. Louis, Mo.

[21] Appl. No.: 962,757

[22] Filed: Oct. 19, 1992

[51] Int. Cl.$^5$ ............................................. F16K 27/08
[52] U.S. Cl. .................. 137/381; 137/614.17; 137/557; 604/119; 251/904
[58] Field of Search ............ 137/614.17, 625.24, 137/557, 381; 251/904, 100; 604/119

[56] References Cited

U.S. PATENT DOCUMENTS

| | | | |
|---|---|---|---|
| 1,088,817 | 3/1914 | Graham | 137/614.17 |
| 1,214,267 | 1/1917 | Block | 137/614.17 |
| 2,791,217 | 5/1957 | Iskander | 128/203 |
| 3,012,752 | 12/1961 | Buck | 251/904 |
| 3,081,770 | 3/1963 | Hunter | 128/221 |
| 3,335,727 | 8/1967 | Spoto | 128/276 |
| 3,395,705 | 8/1968 | Hamilton | 604/119 |
| 3,991,762 | 11/1976 | Radford | 128/276 |
| 4,291,691 | 9/1981 | Cabal et al. | 128/204.18 |
| 4,346,702 | 8/1982 | Kubota | 128/207.14 |
| 4,569,344 | 2/1986 | Palmer | 128/207.14 |
| 4,648,868 | 3/1987 | Hardwick et al. | 604/32 |
| 4,792,327 | 12/1988 | Swartz | 604/119 |
| 4,872,579 | 10/1989 | Palmer | 128/205.19 |
| 5,083,561 | 1/1992 | Russo | 604/119 |
| 5,144,972 | 9/1992 | Dryden | 251/904 |
| 5,215,522 | 6/1993 | Page et al. | 604/33 |

FOREIGN PATENT DOCUMENTS 3347834 4/1985 Fed. Rep. of Germany ...... 604/119

Primary Examiner—A. Michael Chambers
Attorney, Agent, or Firm—Andrew J. Beck; Montgomery W. Smith; Gene B. Kartchner

[57] ABSTRACT

A suction control valve is disclosed which includes a primary suction device access and an ancillary suction device access. The valve includes an actuator which is linearly movable between a first position in which the primary access is closed against suction pressure therethrough, to a second position in which the primary access is open to suction pressure therethrough. The valve also includes a rotatable valve core which can be rotated by the actuator to a third position to disable its linear movement and to open the ancillary access port. When the actuator is in the first position, atmospheric air can pass through the valve and into the suction pressure source in such a manner that a "hissing" auditory signal is generated, indicative of the presence of suction pressure within the valve. When the actuator is in the second or third positions, the "hissing" is prevented.

4 Claims, 5 Drawing Sheets

SUCTION CONTROL VALVE

BACKGROUND OF THE INVENTION

1. Field of the Invention

This invention relates generally to fluid flow valving devices. More specifically, the present invention relates to a valving device for a suction catheter device. Even more specifically, the present invention relates to a suction control valve useable with suction catheters attachable to a respirator manifold of a respiratory system.

2. Prior Art

Respiratory systems used for the ventilation of critically ill patients are now commonly used in medical facilities. Typically, a prior art respiratory system includes a tracheal tube positioned either directly or through the nose or mouth into the trachea of a patient, a manifold connected to the tracheal tube at one port position thereof, and a source of breathable gas connected at a second port thereof. The purpose of the respiration system is to assist the patient in maintaining adequate blood oxygenation levels without overtaxing the patient's heart and lungs.

While a patient is attached to a respiration system, it is periodically necessary to remove fluid from the patient's trachea or lungs. In the past this procedure necessitated disconnections of the respirator system, either by removing the manifold or by opening a port thereof, and insertion of a small diameter suction catheter down the tracheal tube and into the patient's trachea and lungs. The fluid was then suctioned from the patient and the suction catheter was removed and tile respirator system reassembled. Because of the necessary interruption in respiratory support caused by this procedure, a patient's blood oxygen often dropped to an unacceptably low level during the suctioning, even when other previously known breathing assisting efforts were simultaneously provided.

A known solution to the above problem has been to place an additional port on the respirator manifold which is adapted to receive a connector of a suction catheter device. A suction catheter device such as used with this type of respirator manifold is adapted to allow a suction catheter to remain permanently positioned within the manifold without the necessity of attachment or detachment thereof from the manifold in between uses, thereby avoiding substantial manifold pressure loss. The suction catheter device includes an envelope which envelopes the suction catheter in order to prevent contamination of the suction catheter surface which must be repeatedly inserted into and removed from the patient's trachea and lungs. This type of suction catheter device allows continuous respiratory support of the patient during suctioning of fluid from the patient's trachea and lungs, and is commonly controlled by means of a valve located in fluid flow connection between the catheter and the suction source therefore. A valve of this type which is generally exemplary of the prior art is shown in U.S. Pat. No. 4,872,579. The valve selectively communicates vacuum pressure into the interior of a catheter tube when it is desired to evacuate respiratory fluids. The valve is normally biased to a closed position to prevent vacuum flow until a user initiated manual displacement of a valve actuator opens the catheter tube to the vacuum source. The valve actuator is also designed to be rotatable relative to the remainder of the valve from a closed position to a locked position in which actuation for suctioning is prevented.

There nevertheless remain several draw backs associated with suction control valves of the prior art. For example, prior art suction control valves of the above described type fail to provide the user with an auditory indication of the continued availability of suction pressure for use. Further, when it becomes necessary to perform a suctioning procedure on the patient with other than the suction catheter to which the prior art valve is attached, as for example when an oral suctioning device is required for suctioning of the patient's oral cavity, it is necessary with the prior art suction control valves to disconnect the valve and suction catheter entirely from the suction source in order to replace them with the desired oral suctioning device.

OBJECTS AND SUMMARY OF THE INVENTION

A principal object of the present invention is to provide a fluid flow valving device which is designed to provide the user with an auditory signal corresponding to the availability of pressure, including vacuum from a suction source.

Another principal object of the present invention is to provide a fluid flow valving device designed with a locking and unlocking valve actuator which includes an auditory signaling means which informs the user of the locked or unlocked status of the valve.

It is further an object of the present invention to provide a fluid flow valving device which allows attachment of ancillary devices thereto for accessing the pressure or vacuum source without the necessity of removing a primary device therefrom.

Another object of the present invention is to provide a fluid flow valving device as part of a patient aspirating system which can include a primary and/or ancillary device attached thereto such as a suction catheter and/or a Yankauer device, and allow access to the patient's oral cavity, trachea, or lungs, without interruption of continuous patient respiratory support.

A further object of the present invention is to provide a fluid flow valving device which is designed to allow attachment thereto of primary and ancillary devices such as a primary suction catheter device and an ancillary Yankauer suctioning device, which allows complete opening or closure of the primary device in isolation from the ancillary device, whereby the fluid flow valving device functions only as a connector of the ancillary device to the suction source and thus avoids any necessity of removing the fluid flow valving device from the suction source in order to attach the primary or ancillary device thereto, or to change from the use of one to the other.

These and other objects of the present invention are realized in a presently preferred embodiment thereof, described by way of example and not necessarily by way of limitation, which includes a fluid flow valving device for controlling suction through a preferred primary device, shown for purposes of description as a suction catheter device, and provides a connection port for an ancillary device such as a Yankauer suction wand.

The valve includes a main body forming a fluid flow channel therethrough and includes an actuator for opening and closing the fluid flow passage of the main body. The actuator is normally biased to a position in which the fluid flow passage is closed to prevent fluid passage therethrough and can be actuated by the user against the biasing thereof in order to open the fluid flow passage. The actuator may also be rotated relative to the valve body to a locked position in which the actuator can no longer be actuated to cause fluid flow through the valve. A tubular extension for attachment of the valve to a suction source and to a primary device is included on each end of the fluid flow channel through the valve body.

The valve body also includes an ancillary device connection port positioned opposite the valve actuator which is normally closed with a flip top cap and can be opened to expose a connection port which is designed to receive an ancillary device such as a Yankauer suctioning wand therein. The port is placed in fluid flow connection with the fluid flow passage through the valve body when the actuator is rotated to the locked position, which in turn is in fluid flow connection with the suction source to which the valve is attached.

DETAILED DESCRIPTION OF THE PREFERRED EMBODIMENT

Figure 1:
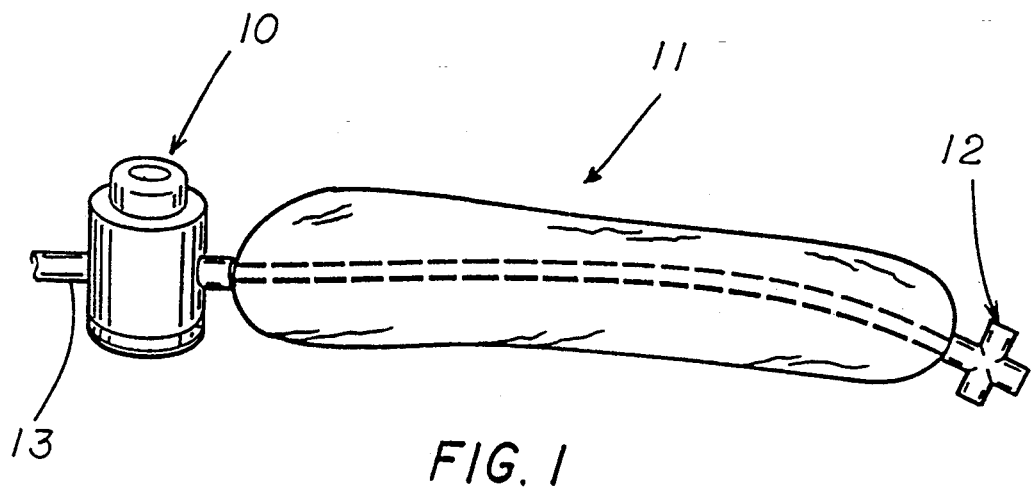
FIG. 1 shows a perspective view of a fluid flow valving device formed in accordance with the principals of the present invention attached to a suction source and a suction catheter device designed for use with a respiratory support system.

As shown in the exemplary drawings for the purposes of illustration, an embodiment of a fluid flow valving device made in accordance with the principals of the present invention, referred to generally by the reference numeral 10, is provided for attachment to a suction source and a primary suctioning device and, when desired, to an ancillary suctioning device.

More specifically, as shown in FIG. 1, the suction control valve 10 is shown attached to a suction catheter device 11 which is adapted to be used in conjunction with a patient respiratory support system through attachment to a respirator manifold such as the manifold 12. The valve 10 is also shown attached to a source of suction pressure (not shown) by means of a suction tube 13.

Figure 2:
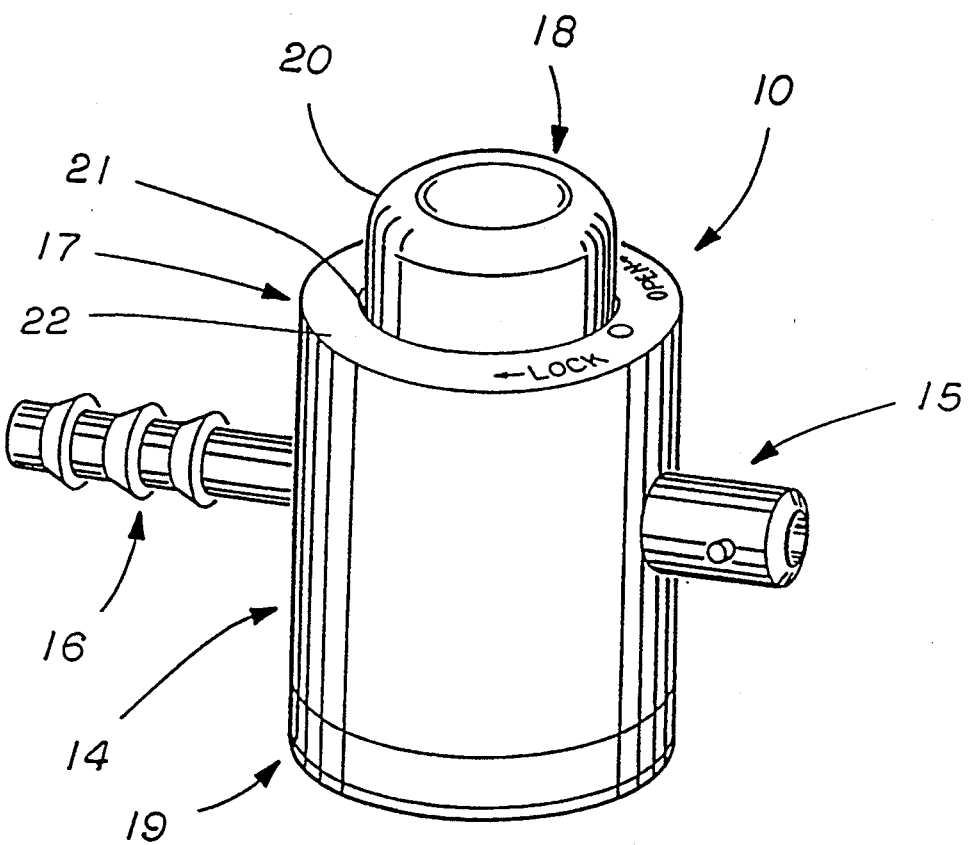
FIG. 2 is a perspective view of a fluid flow valving device formed in accordance with the principals of the present invention.

As shown in FIG. 2, the valve 10 of the present invention is formed of a valve housing 14 with a primary device connector 15 extending away therefrom in a radial direction and a suction pressure source connector 16 extending away therefrom in a radial direction opposite the primary device connector 15. A lower cap 19 having the same diameter as the valve housing 14, covers the bottom of the valve housing 14. An upper cap 17 is connected to the top of the valve housing 14. A portion of the actuator 18 (constituting the button 20) extends from the interior of the valve housing 14 through the upper cap opening 21 and above the annular surface 22 of the upper cap 17. The positioning of the actuator 18 on the valve 10 is intended to allow for ease of manipulation thereof in a single hand of the user. The valve 10 is sized so as to be easily placeable within a user's palm such that the user's thumb may rest comfortably on the button 20 of the actuator, with the user's fingers curling about the lower cap 19 to support the valve 10 against the internal bias of the actuator 18 when the user presses on the button 20 to open a suction channel through the valve 10.

Figure 3:
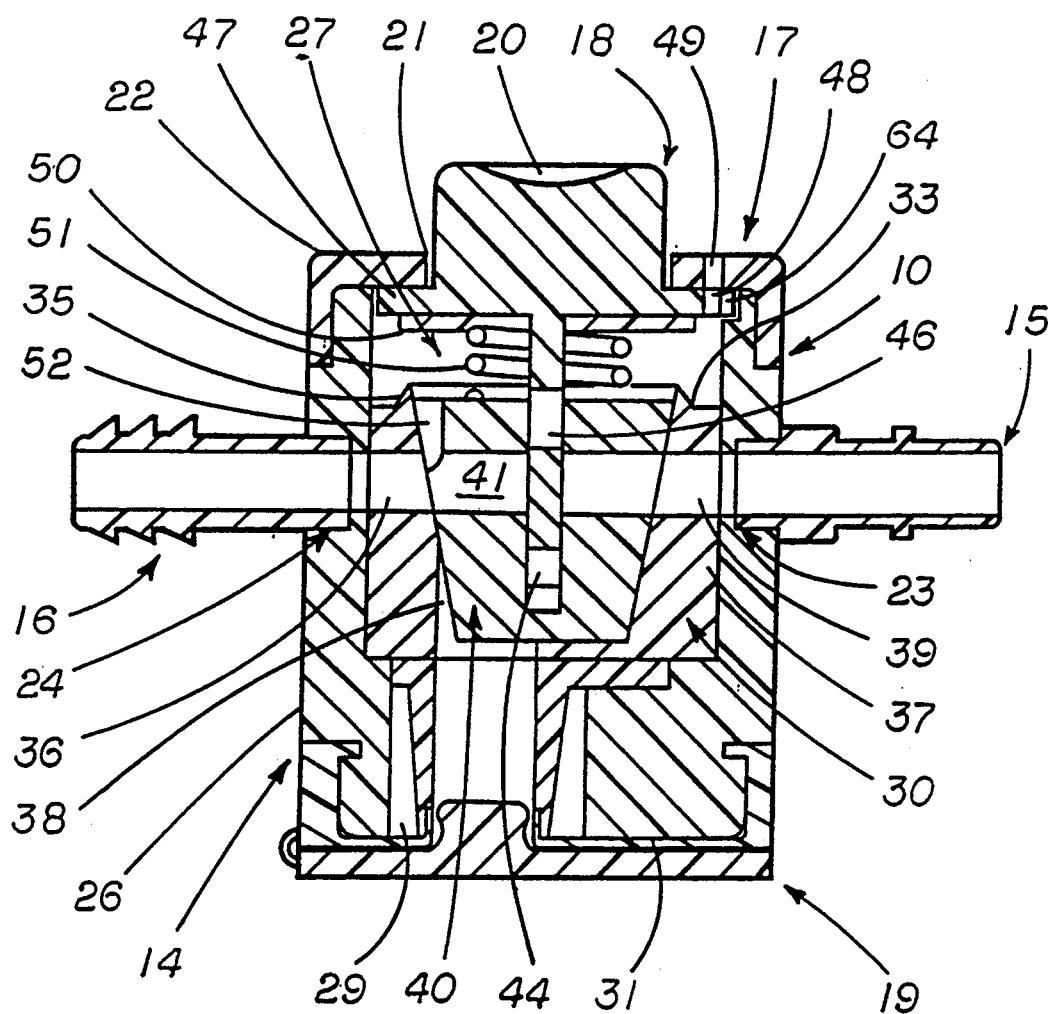
FIG. 3 is a cross-sectional view of the fluid flow valving device of FIG. 2.

Referring now to FIG. 3, the preferred internal structural arrangement of the valve 10 of the present invention will be explained, with the aid of FIGS. 4–6 which show various views of individual component.

Figure 4:
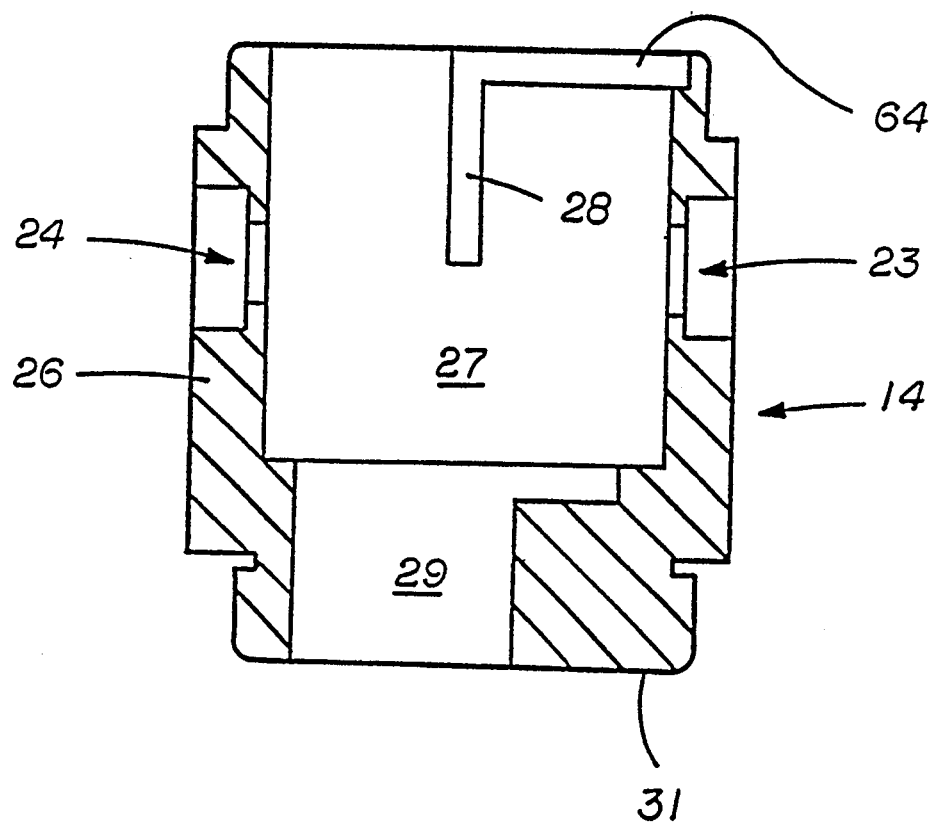
FIG. 4 is a cross-sectional view of the valve housing of the fluid flow valving device of the present invention.

Referring specifically to FIGS. 3 and 4, the valve housing 14 is formed generally into a hollow cylindrical shape and includes a primary device connector opening 23 and a suction source connector opening 24 which are formed through the side wall 26 at diametrically opposed positions and which pass into the large cylindrical chamber 27. The openings 23 and 24 each allow attachment of the primary device connector 15 and the suction source connector 16 respectively to the valve housing 14.

The large cylindrical chamber 27 includes a longitudinally oriented groove 28 (best shown in FIG. 4) which aligns with a hub (not shown) on the valve body 30 when the valve body 30 is inserted thereinto in order to ensure their proper relative orientation for use.

The housing 14 also includes a small cylindrical chamber 29 which opens into the large cylindrical chamber 27 and is open through the bottom 31 of the housing 14, which forms part of the ancillary fluid flow channel through the valve 10 as will be explained below.

Figure 5:
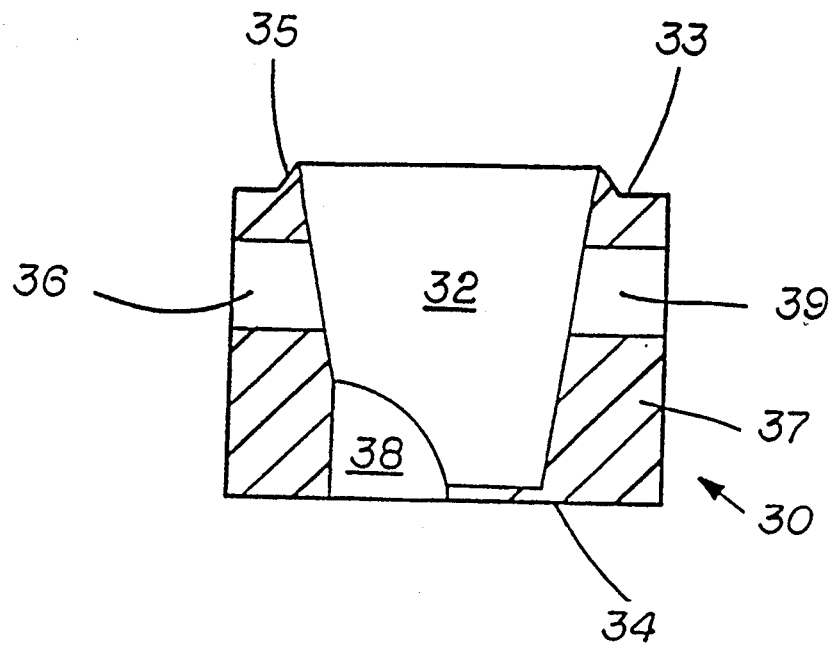
FIG. 5 is a cross-sectional view of the valve body of the fluid flow valving device of the present invention.

As best seen in FIGS. 3 and 5, the valve body 30 is a generally cylindrical member having a plurality of openings therethrough. First, a generally conically shaped bore 32 is formed through the top surface 33 and extends nearly to the bottom surface 34 thereof. The conical bore 32 is surrounded at its opening adjacent the top surface 33 by an annularly shaped protrusion or seat 35. A cylindrical fluid flow channel, identified for simplicity of later explanation of operation of the valve 10 as elements 36 and 39, passes through the valve body 30 and completely through the side wall 37 thereof. The channel 36,39 is oriented such that its longitudinal axis perpendicularly intersects with the longitudinal axis of the conical bore 32. A second cylindrical fluid flow channel 38, generally perpendicular to the first fluid flow channel 36,39 passes through the bottom 34 of the valve body 30 into the conical bore 32.

Figure 6:
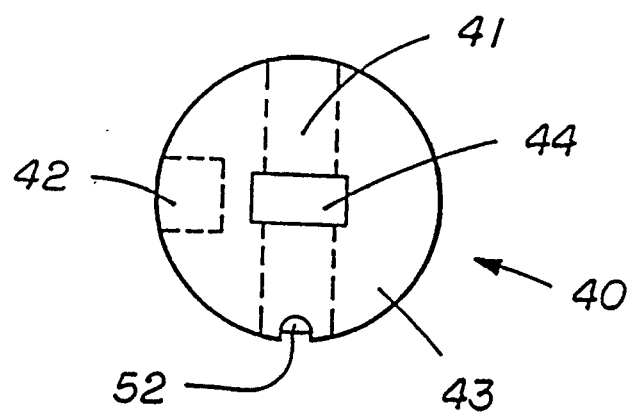
FIG. 6 is a top view of the rotatable core of the fluid flow valving device formed in accordance with the principals of the present invention.

As best seen in FIGS. 3 and 6, the core 40 rests within the conical bore 32, and is generally conical in shape to match the shape of the conical bore 32. The core 40 forms several channels therethrough which can be positioned for operation of the valve 10 by rotation of the core 40 relative to the body 30 in the manner as will be described below.

Figure 7:
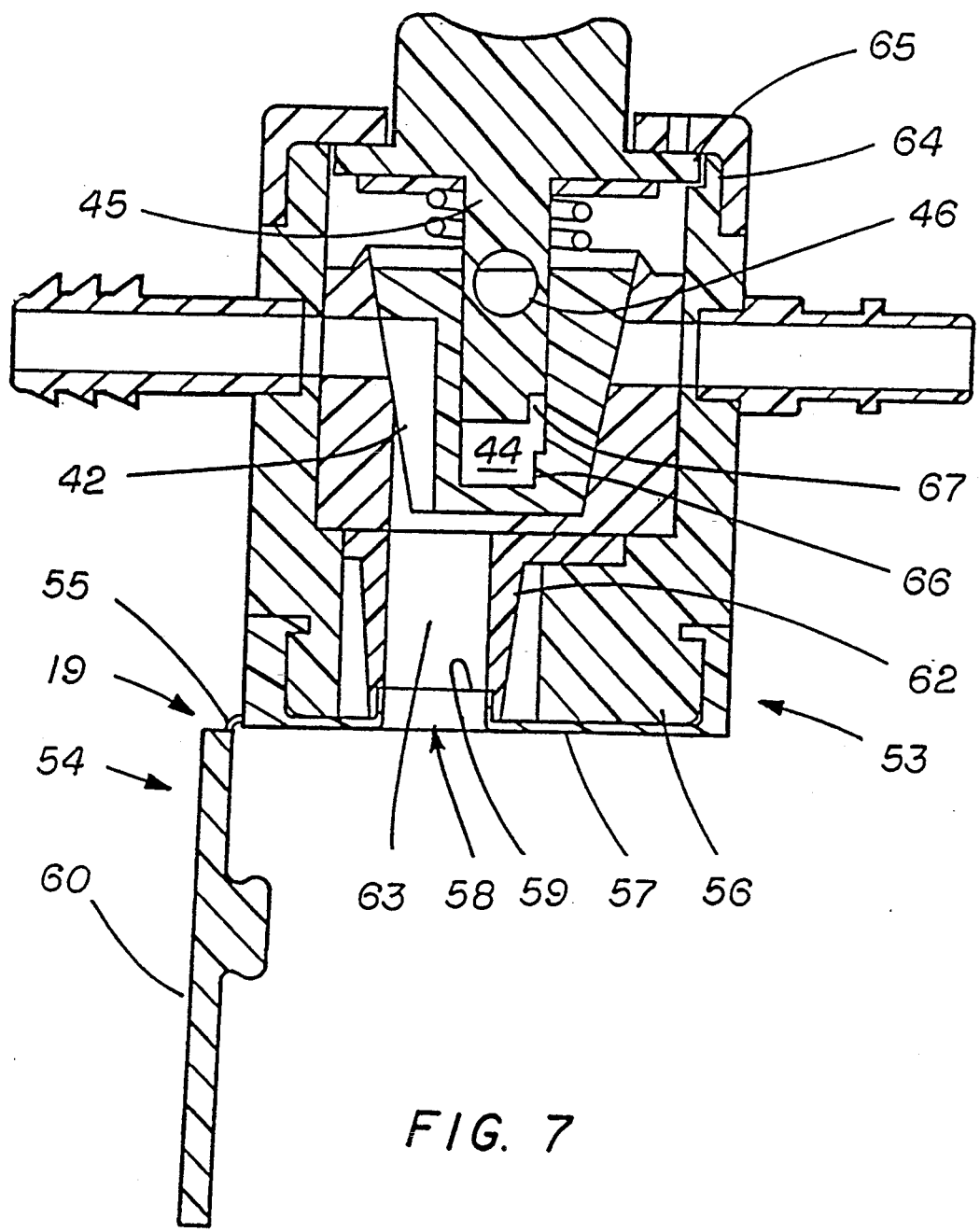
FIG. 7 is a cross-sectional view of the fluid flow valving device as shown in FIG. 3, modified to show the actuator and core rotated to the locked position.

A primary fluid flow channel 41 is formed through the core 40 so as to match the diameter of, and be alignable with, the fluid flow channels 36 and 39 in the body 30. An ancillary fluid flow channel 42 (best shown in FIGS. 6 and 7) attaches fluid flow channel 36 with the second cylindrical fluid flow channel 38. The ancillary fluid flow channel 42 is positioned about the core 40 so as to be oriented approximately one quarter of the way around the circumference of the core from the primary fluid flow channel 41, or in other words (as best seen in FIG. 6) the position of the ancillary fluid flow channel 42 is approximately 90° around the surface 43 of the core 30 from the primary fluid flow channel 41. The relative positioning of the primary and ancillary fluid flow channels 41 and 42 respectively, allow positioning of the core 40 in a first position (shown in FIG. 3) in which the primary fluid flow channel 41 is oriented for fluid flow between fluid flow channels 36 and 39, and a second position (as shown in FIG. 7) in which it is rotated 90° from the first position and in which the ancillary fluid flow channel 42 thereof is in alignment between fluid flow channel 36 and the second cylindrical fluid flow channel 38. The operation of the valve 10 with respect to each position of the core 40 will be explained in detail momentarily.

The core 40 includes a bleed channel 52 which extends from the top surface 43 of the core 40 into the first fluid channel 41.

The core 40 also includes a rectangularly shaped slot 44 which passes through the top surface 43 of the core and bisects the first fluid flow channel 41. As can be seen in FIGS. 3 and 7, the slot 44 accommodates the actuator extension 45 for sliding movement therein between a first position in which the extension 45 blocks flow through the first fluid flow channel 41, and a second position in which the actuator 18 is forced downwardly to move the actuator opening 46 into alignment with the first fluid channel 41.

The extension 45 also allows the actuator 18 to effect rotation of the core 40 when the button 20 of the actuator is rotated relative to the valve 10. Rotation of the core 40 between the first or open position as shown in FIG. 3, and the lock position shown in FIG. 7, is caused by rotation of the button 20 relative to the valve 10 approximately one quarter turn. The valve 10 may include markings such as on the surface 22 of the upper cap 17 (as shown in FIG. 2) and/or on the button 20, to indicate the position of the core 40 for proper operation of the valve.

As shown in FIG. 3, the actuator 18 includes a shoulder 47 which is sized to fit within the large cylindrical chamber 27 of the housing 14 to be held in place there within by the upper cap 17. The shoulder 47 forms a slot 48 therethrough which is located adjacent the opening 49 in the upper cap 17 when the actuator 18 is in its first or open position. The shoulder 47 also includes a tab 65 (shown only in FIG. 7) which is positioned around the circumference of the shoulder 47 approximately 90° away from the slot 48. The tabs 65 rides in the slot 64 (best shown in FIG. 4) formed around one quarter (90°) of the internal circumference of the large cylindrical chamber 27 of the housing 14 and joins with the longitudinally oriented groove 28. As is evident, the tab 65 allows the actuator 18 to rotate only a quarter turn, since it is inhibited from further rotation by the ends of the slot 64. In FIG. 3 for example, the tab 65 is rotated to the end of slot 64 which is adjacent the longitudinal groove 28. In this position, the slot 48 through the shoulder 47 of the actuator button 20 is positioned adjacent the opening 49 in the upper cap 17. In FIG. 7, the tab 65 is rotated one quarter of a turn to the opposite end of slot 64 and is positioned directly adjacent the opening 49 in the upper cap 17. It should be noted that the width of the tab 65 is less than the width of the groove 28 so that the tab 65 may pass downwardly therethrough whenever it is aligned therewith and the button 20 of the actuator 18 is pushed down. As is readily evident therefor, only single rotational position of the actuator 18 allows downward movement thereof, this being defined as the "open" position where the tab 65 is aligned with the groove 28.

Referring again to FIG. 3, a flexible, soft elastomeric pad 50 of generally circular shape is affixed to the actuator 18 below the shoulder 47 and is of a slightly larger diameter than the diameter of the seat 35 protruding from the surface 33 of the body 30. A compression spring 51 is positioned between the top surface 43 of the core 40 and the shoulder 47 and operates to hold the actuator 18 in its uppermost position where the actuator shoulder 47 abuts the upper cap 17.

The fluid flow passage formed by the suction source connector 16, the fluid flow channels 36, 41, 39, and the primary device connector 15, forms essentially an elongate linear channel of uniform diameter passing entirely through the valve 10. When the actuator opening 46 is moved downwardly to be positioned within the primary fluid flow channel 41, it is readily apparent that a single linear fluid flow channel of uniform diameter through the entire valve 10 is formed which does not cause any obstruction or blockage of fluid passing through the valve 10. In this manner, mucal material, including clotted material referred to generally as mucus plugs, encounters no obstruction as it is drawn through the valve 10, and therefore is not likely to cause blockage of the valve during use.

As shown in FIGS. 3 and 7, the bottom of the valve housing 14 is covered with a lower cap or "flip cap" 19. The lower cap 19 is formed of a generally cylindrical shape having a diameter equal to the diameter of the valve housing 14 and includes a fixed member 53 which is hingeably attached to a cover member 54 by means of hinge 55 which may be of the "living hinge" type and formed of polymeric material. The fixed member 53 is preferably attached to the annular base 56 of the valve housing by a snap fit or an ultrasonic weld, however any well known attachment means may be used. The fixed member 53 includes a circular plate 57 which has an opening 58 formed centrally therein which is surrounded by an inwardly projecting boss 59. The cover member 54 also includes a circular plate 60, on the interior surface of which a plug 61 is formed and sized so as to fit snugly within the fixed member opening 58 to form a fluid tight seal whenever the cover member 54 is closed over the fixed member 53.

A bushing 62 is located within cylindrical chamber 29 of the valve housing 14 between the body 30 and the circular plate 57. The bushing 62 forms a fluid flow channel 63 therethrough which is shaped on one end thereof to connect with boss 59 on the circular plate 57 and on the other end to align with the second cylindrical fluid flow channel 38 of the body 30 in fluid tight relationship, thus allowing fluid flow connection of the bushing fluid flow channel 63 with the suction source through the ancillary fluid flow passage 42.

The bushing 62 is preferably formed of a soft polymeric material which can be deformed to accept and hold a relatively rigid connector of an ancillary device, such as the end connector of a Yankauer suctioning wand (not shown).

OPERATION OF THE PREFERRED EMBODIMENT

As shown in FIG. 1, preparation for operation of the valve 10 of the present invention includes attaching the primary device connector 15 thereof to the distal end of a primary device such as the suction catheter device 11, and attaching the suction source connector 16 to a suction tube 13 from a suction-pressure source. When it is desired to administer suction to a patient, the suction catheter of the suction catheter device 11 is inserted through the manifold 12 into the patient's trachea or lungs, and the button 20 of the actuator 18 is rotated to the unlocked or opened position as best shown in FIG. 3.

When in the first or open position, the actuator 18 allows a bleed of suctioned atmospheric air to pass into the valve 10 through the cap bleed opening 49 and move past the actuator shoulder slot 48 into the large cylindrical chamber 27 of the valve housing 14 where it is then drawn through the core bleed channel 52 into the primary fluid flow channel 41 of the core 40 and from there through channel 36 and into the suction source connector 16 where it can be drawn out of the valve 10 into the suction pressure source.

Movement of atmospheric air through the valve 10 to the suction source when the actuator 18 is in the open position generates an auditory signal, being a very recognizable "hissing" sound, which is indicative of the operation of the suction pressure source and the presence of suction pressure within the valve 10.

When it is desired to initiate suctioning through the suction catheter device 11, the user forces the actuator button 20 downwardly into the valve housing 14 against the bias of the compression spring 51. This linear translational movement of the actuator 18 relative to the valve housing 14 causes the actuator extension 45 to move downwardly within the core slot 48. This causes the actuator opening 46 to move into alignment with the primary fluid flow channel 41 of the core 40. No resistance of downward movement of the actuator 18 is caused by the tab 65, since it is aligned with groove 28 and can therefore pass downwardly therein.

As can be seen, although the actuator extension 45 blocks the fluid flow channel 41 whenever the actuator 18 is in its fully upwardly extended or "released" position, it gradually moves out of blocking position as the actuator opening 46 is moved into alignment position with the primary fluid flow channel 41 as the actuator button 20 is depressed. As is also readily evident, the amount of suction pressure allowed through the fluid flow channel 41 can be regulated from a "no flow" level when the button 20 is released, to gradually increasing flow levels as the actuator opening 46 is moved into alignment with the fluid flow channel 41 as the button 20 is depressed toward the body 30.

As can be seen, complete depression of the button 20 occurs when the pad 50 on the actuator shoulder 47 contacts and seals against the seat 35 of the body 30. In the completely depressed position, the actuator opening 46 is completely aligned with the fluid flow channel 41 and presents no fluid flow obstacle therethrough.

It should be noted that when the actuator 18 is completely depressed until the pad 50 seals against seat 35 causing complete alignment of the actuator opening 46 with the primary fluid flow channel 41, fluid flow caused by the suction pressure source is allowed to pass directly through the valve 10 in a completely open and linear flow path, having no element of the valve 10 obstructing the passage of flow therethrough. This is especially useful in the preferred intended use of the valve 10 of the present invention of suctioning fluids from a patient's trachea and lungs, since it affords the clearest possible passageway through the valve 10 for fluids normally suctioned from the patient. Even clotted mucal material can pass easily through the valve 10 without the risk of clogging the fluid flow passages therethrough since there are no obstructing valve elements.

Complete depression of the button 20 causes the pad 50 to seal against seat 35 and block the flow of atmospheric air through bleed channel 52. Thus, whenever the actuator button 20 is depressed, bleeding of atmospheric air into the primary fluid flow channel 41 is prevented. This causes the "hissing" of the valve 10 to stop, which provides the user with another audio indication of the proper operation of the valve 10. The user immediately recognizes the arresting of the "hissing" sound upon depression of the actuator button 20, which signals the user that the suction pressure has been diverted into the suction catheter device 11. In this way, the presence or absence of the "hissing" sound provided by the valve 10 of the present invention assists the user in confirming proper operation of the valve 10.

When the actuator button 20 is released after suctioning through the suction catheter device 11 is completed, the actuator opening 46 moves upwardly, due to the bias of the compression spring 51, to again allow atmospheric air to pass through the valve 10, and generate the "hissing" auditory signal. Upward movement of the actuator 18 is arrested by the abutment of the actuator shoulder 47 against the upper cap 17.

At times it is convenient, and even important from a safety consideration for a patient, to ensure that depression of the actuator button 20 cannot allow suction pressure through the suction catheter device 11. If it is desired to prevent suctioning through the suction catheter device 11, the user may rotate the actuator 18, by rotating actuator button 20, approximately one quarter turn to the locked position.

As best shown in FIG. 7, one quarter rotation of the actuator 18 causes the core 40 to also rotate within the body 30 approximately one quarter turn. In this position, the ancillary fluid flow channel 42 is positioned in direct alignment with the fluid flow channel 36 of the body 30, and any incidental depression of the actuator button 20 when in this locked position will fail to allow fluid flow through the first fluid flow passage 41, since it has been moved out of alignment with fluid flow channel 36. Therefore, no suction pressure can be applied to the suction catheter device 11.

Further, whenever the actuator 18 has been rotated to the locking position, the bleed channel 52 of the core 40 is also rotated out of alignment with the fluid flow channel 36. Therefore, bleed of atmospheric air into the primary fluid flow passage 41 is prevented, and the user is aware of such by the arresting of the "hissing" auditory signal.

This feature of the present invention allows a user to lock the actuator 18 against accidental suctioning through the suction device 11 (such as may occur if the valve 10 and suction catheter device 11 are left unattached while attached to a respiratory support system on a patient). Although a patient may inadvertently depress the actuator 18, for example, by accidentally rolling over on top of the valve 10, suctioning of fluid through the suction catheter device 11 cannot occur since the actuator 18 is in the locked position, with tab 65 thereof rotated out of position with groove 28 of the valve housing 14, and the core 40 rotated to block fluid flow through channel 39.

Further, medical personnel or other users of the valve 10 will be provided with an auditory signal (absence of hissing) whenever the valve 10 is locked against actuation, and a different auditory signal (the presence of hissing) whenever the valve 10 is unlocked or opened. This can be extremely convenient and add an additional safety factor to the use of the valve 10 in that it is not necessary for the user to see directly whether or not the valve 10 is locked against actuation, because an auditory hissing signal is generated whenever the valve 10 is open, which signals the user that the valve 10 must either be attended to, or locked, in order to avoid possible injury to the patient.

The valve 10 of the present invention may also operate as a connector for an ancillary suctioning device such as a Yankauer suction wand (not shown) if desired. As shown in FIG. 7, when it is desired to attach an ancillary device to the valve 10 of the present invention, the user merely rotates the cover member 54 of the lower cap 19 to an open position. The end connector of the Yankauer suction wand or other ancillary device is then inserted through the fixed member circular plate opening 58 and into the bushing fluid flow channel 63 to generate a friction fit therewith to hold the Yankauer in connection with the valve 10. As can be seen, attachment of a Yankauer in this manner provides immediate connection thereof with the suction pressure source attached to the valve 10 through the bushing fluid flow channel 63 and the valve housing fluid flow channel 36 whenever the actuator 18 is in the locked position.

Attachment of an ancillary device to the valve 10 without requiring detachment of the primary device 11 therefrom can be very important in many procedures involving suctioning of fluids from a patient attached to a respiratory support system. Since serious detriment to the patient can occur whenever it is necessary to breach the integrity of the respiratory support system, the avoidance of disassembly of any equipment thereof, or detachment of the suction source, becomes a positive procedural improvement.

As can be seen with the present invention, the ability to attach a Yankauer suction wand to the valve 10 to allow suctioning of the patient's oral cavity without the necessity of disassembling any part of the system in place for primary suctioning of the patient's trachea and lungs is an important improvement over the prior art.

When the Yankauer suction wand is no longer needed, it can be detached from the valve 10 and the cover member 54 can again be closed to block the bushing fluid flow channel 53 and seal it against fluid flow therethrough.

It should be noted that suctioning through the ancillary port connection of the valve 10 can only be accomplished when the actuator 18 is in the locked position, with the ancillary fluid flow channel 42 oriented for fluid flow with the fluid flow channel 36.

It should also be noted that all internal components of the valve 10, including the actuator 18, core 40, body 30, and bushing 62 are designed such that assembly thereof into the valve housing 14 is substantially simplified. In each instance, the particular element to be assembled into the valve housing 14 has been designed to the extent possible to allow only the element to fit within the valve housing 14 only when it is properly positioned for assembly. Specifically, the bushing 62 is formed asymmetrically to allow only one possible positioning thereof within the small cylindrical chamber 29. The body 30 includes a nub (not shown) which must be aligned with groove 28 in order for the body 30 to be insertable within the large cylindrical chamber 27. The core 30 includes a step 66 in the bottom of the slot 44 thereof which accommodates the actuator extension 45 forces proper alignment of the actuator extension 45 therein by allowing proper operation only when shoulder 67 of the extension 45 is oriented in alignment therewith. The actuator 18/core 30 sub-assembly can only be positioned within the valve housing 14 such that the tab 65 of the shoulder 47 of the actuator button 20 is positioned within the slot 64 of the housing 14. Although various methods and means for ensuring proper assembly of the valve 10 of the present invention have been shown, it should be understood that other means and methods known in the art could also be employed without departing from the spirit and scope of the present invention.

It will be also apparent from the foregoing that, while a particular embodiment of the present invention has been illustrated and described, various modifications can be made thereto without departing from the spirit and scope of the invention. Accordingly, it is not intended that the invention be limited, except as by the appended claims.

I claim:

1. A suction control valve comprising:
   a valve body having a suction source access port, a primary suction device access port, and a fluid flow passage for allowing fluid flow passage between said suction source access port and said primary suction device access port,
   an ancillary suction device access port in fluid flow connection with said fluid flow passage, and
   an actuator positioned at least partially within said valve body for movement relative thereto between at least a first position in which said primary suction device access port and said ancillary suction device access port are closed against fluid flow therethrough, a second position in which said primary suction device access port is open to fluid flow therethrough and said ancillary suction device access port is closed to fluid flow therethrough, and a third position in which said primary suction device access port is closed against fluid flow therethrough and said ancillary suction device access port is open to fluid flow therethrough.

2. A suction control valve according to claim 1 wherein said ancillary suction device access port includes a cap independent of said actuator for opening and closing said ancillary suction device access port for fluid flow therethrough.

3. A suction control valve according to claim 1 wherein said ancillary suction device access port includes a relatively flexible bushing forming a fluid flow channel therethrough which is in fluid flow connection with said fluid flow passage, said bushing being held within said valve body by said cap.

4. A suction control valve according to claim 3 wherein said cap includes a cover member hingeably moveable between a closed position and an open position, whereby said cover member inhibits fluid flow through said bushing fluid flow channel when in said closed position, and allows insertion of an ancillary suction device into said bushing fluid flow channel when in said open position.

* * * * *